(12) United States Patent
Hayashi et al.

(10) Patent No.: US 8,790,620 B2
(45) Date of Patent: Jul. 29, 2014

(54) RADIOACTIVE DIAGNOSTIC IMAGING AGENT

(75) Inventors: Akio Hayashi, Chiba (JP); Toshiyuki Shinmura, Chiba (JP); Daisaku Nakamura, Chiba (JP); Soichi Takasaki, Chiba (JP); Shinji Tokunaga, Chiba (JP); Emi Kaneko, Chiba (JP); Masahito Toyama, Chiba (JP)

(73) Assignee: Nihon Medi-Physics Co., Ltd., Tokyo (JP)

( * ) Notice: Subject to any disclaimer, the term of this patent is extended or adjusted under 35 U.S.C. 154(b) by 218 days.

(21) Appl. No.: 12/518,307

(22) PCT Filed: Nov. 20, 2007

(86) PCT No.: PCT/JP2007/072444
§ 371 (c)(1),
(2), (4) Date: Jun. 16, 2009

(87) PCT Pub. No.: WO2008/075522
PCT Pub. Date: Jun. 26, 2008

(65) Prior Publication Data
US 2010/0028258 A1 Feb. 4, 2010

(30) Foreign Application Priority Data

Dec. 21, 2006 (JP) ................. 2006-343753

(51) Int. Cl.
| | | |
|---|---|---|
| A61K 51/00 | (2006.01) | |
| A61M 36/14 | (2006.01) | |
| A61K 49/04 | (2006.01) | |
| A61K 47/26 | (2006.01) | |
| A61K 51/04 | (2006.01) | |

(52) U.S. Cl.
CPC ............ *A61K 49/0433* (2013.01); *A61K 47/26* (2013.01); *A61K 51/04* (2013.01)
USPC ...................................... 424/1.65; 424/1.89

(58) Field of Classification Search
CPC .... A61K 47/26; A61K 51/04; A61K 49/0433
USPC ...................................................... 424/1.89
See application file for complete search history.

(56) References Cited

U.S. PATENT DOCUMENTS

| | | | |
|---|---|---|---|
| 5,679,665 A | * | 10/1997 | Bergamini et al. ........... 514/171 |
| 6,017,706 A | | 1/2000 | Parshad et al. |
| 6,027,710 A | | 2/2000 | Higashi et al. |
| 6,045,773 A | * | 4/2000 | Isakson et al. ............... 424/1.81 |
| 6,562,579 B1 | * | 5/2003 | Yu et al. ......................... 435/7.1 |
| 6,713,042 B2 | * | 3/2004 | Liu ............................... 424/1.65 |
| 7,264,792 B2 | | 9/2007 | Gibson et al. |
| 2005/0175536 A1 | | 8/2005 | Knight Castro |
| 2006/0039855 A1 | | 2/2006 | Gibson et al. |
| 2006/0292073 A1 | | 12/2006 | Goodman et al. |
| 2008/0076914 A1 | | 3/2008 | Grigg et al. |
| 2010/0119448 A1 | | 5/2010 | Nakamura et al. |

FOREIGN PATENT DOCUMENTS

| | | |
|---|---|---|
| EP | 0 832 654 A2 | 4/1998 |
| EP | 0832654 A2 | 4/1998 |
| EP | 1 356 827 A1 | 10/2003 |
| JP | H10-147542 A1 | 6/1998 |
| JP | 2006-500319 A1 | 1/2006 |
| JP | 2006-510706 A1 | 3/2006 |
| WO | WO 03/090789 A1 | 11/2003 |
| WO | 2004/056725 A1 | 7/2004 |
| WO | WO 2004/056725 A1 | 7/2004 |
| WO | 2006/037950 A1 | 4/2006 |
| WO | WO 2006/126410 A1 | 11/2006 |
| WO | 2008/099800 A1 | 8/2008 |

OTHER PUBLICATIONS

Mannitol Drug (created on Jun. 13, 2005, p. 1-7).*
McConathy et al. (Appl. Rad. Isot. 2003, 58, 657-666).*
Moore, J.S., et al., Protection of protein A-Sepharose columns irradiated to sterilization doses, Radiation Physics and Chemistry, 47(1):161-5 (1996).
Office Action, dated Aug. 10, 2010, in corresponding Chinese Application 2007800473763.9 (in English translation).
Supplementary European Search Report, dated Oct. 26, 2010 in EPO Application 08863261.7.
Office Action dated Oct. 1, 2010, in Russian Application 2008126277/04(032044) (Russian translation).
Communication from European Patent Office in EP Application 06833463.0, dated Jul. 14, 2010.
Examination Report issued Feb. 17, 2010 in New Zealand Application No. 568179.
Lijuan J. Wang et al., "Syntheses of New Conformationally Constrained S-[2-[(1-Iminoethyl) amino]ethyl]homocysteine Derivatives as Potential Nitric Oxide Synthase Inhibitors", Heteroatom Chemistry, vol. 13, No. 1, pp. 77-83 (2002).
Laurent Martarello et al., "Synthesis of syn* and anti-1-Amino-3[18F]fluoromethyl-cyclobutane-1-carboxylic Acid (FMACBC), Potential PET Ligands for Tumor Detection", *Journal of Medicinal Chemistry*, vol. 45, No. 11, pp. 2250-2259 (2002).
Timothy M. Shoup et al., "Synthesis of [$^{18}$F]1-Amino-3-fluorocyclobutane-1-carboxylic Acid (FACBC): A Pet Tracer for Tumor Delineation", *The Journal of Labelled Compounds and Radiopharmaceuticals*, 42(3):215-225 (1999).
Timothy M. Shoup et al., "Synthesis and Evaluation of [$^{18}$F]1-Amino-3-fluorocyclobutane-1-carboxylic Acid to Image Brain Tumors", *The Journal of Nuclear Medicine*, vol. 40, No. 2, pp. 331-338 (1999).
Second Office Action dated Apr. 14, 2011 against Chinese counterpart Application No. 20078004363.9 (Chinese/ English translation).
Office Action dated (21 MAP 2011) against Russian counterpart Application No. 2009128055/15(038991) (Russian/ English translation).

(Continued)

*Primary Examiner* — Michael G Hartley
*Assistant Examiner* — Melissa Perreira
(74) *Attorney, Agent, or Firm* — Fitch, Even, Tabin & Flannery LLP

(57) ABSTRACT

A composition including a radioactive fluorine-labeled amino acid compound is provided, which can be prevented from radiolysis. Disclosed is a composition which includes a solution containing a radioactive fluorine-labeled amino acid compound as an effective ingredient, in which the pH value of the solution is kept at 2.0-5.9, more preferably 2.0-4.9 in order to inhibit radiolysis. Also, it is possible to further inhibit radiolysis by adding thereto a pharmaceutical additive capable of inhibiting radiolysis, such as a sugar, a sugar alcohol and a sugar lactone, while the pH is kept at 2.0-5.9.

11 Claims, 1 Drawing Sheet

(56) References Cited

OTHER PUBLICATIONS

Office Action, dated May 26, 2011, in corresponding Russian Application 2009128055/15(038991).

Office Action dated Jun. 27, 2012, issued in Australian application 2007335633.

Australian Office Action dated Feb. 11, 2013, issued against corresponding Australian Patent Application No. 2007335633, entire document, 3 pages.

Canadian Office Action dated Sep. 26, 2013, in Canadian Application No. 2,672,262 (2 pages).

Sara Goldstein et al., "Mannitol as an OH scavenger in aqueous solutions and in biological systems", International Journal of Radiation Biology, 1984, vol. 46, No. 6, pp. 725-729.

Margaret Cm Vissers et al., "Oxidative Damage to Fibronectin II. The Effects of Hydrogen Peroxide and the Hydroxyl Radical", Archives of Biochemistry and Biophysics, vol. 285, No. 2, 1991, pp. 357-365.

J.S. Moore et al., "Protection of Protein A-Sepharose Columns Irradiated to Sterilization Doses", Radiation Physics and Chemistry, Elsevier Science Publishers, vol. 47, No. 1, Jan. 1996, pp. 161-165.

European Search Report dated Jan. 30, 2013, issued against European Patent Application 07832174.2.

Supplemental European Search Report dated Feb. 18, 2013, issued against European Application No. 07832174.2.

KR Office Action 10-2009-7010980 dated Mar. 26, 2014.

\* cited by examiner

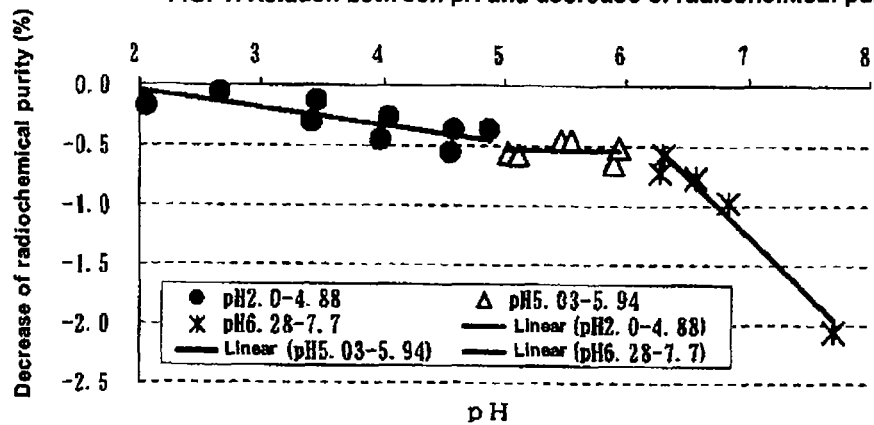
FIG. 1: Relation between pH and decrease of radiochemical purity
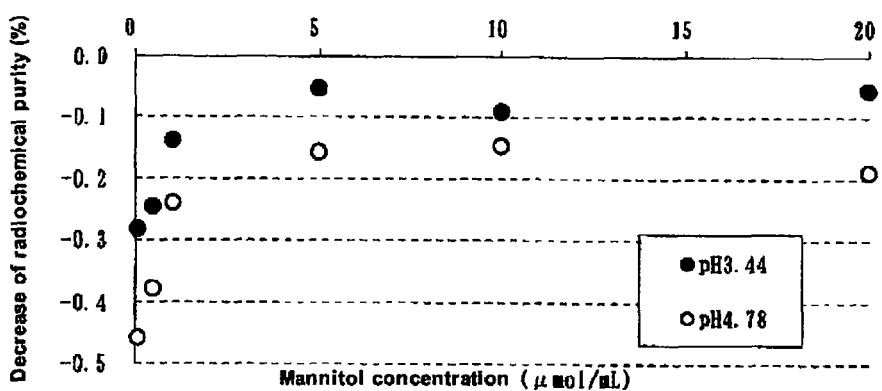
FIG. 2: Relation between mannitol concentration and decrease of radiochemical purity

RADIOACTIVE DIAGNOSTIC IMAGING AGENT

CROSS-REFERENCE TO RELATED APPLICATIONS

This is a U.S. National Phase of International Application PCT/JP2007/072444, filed Nov. 20, 2007, and claims foreign priority under 35 U.S.C. §119 based on Japanese Application No. 2006-343753, filed Dec. 21, 2006, the entire disclosures of which are hereby incorporated herein by reference.

TECHNICAL FIELD

The present invention relates to a composition of a radioactive fluorine-labeled amino acid compound. More specifically, it relates to a composition of a radioactive fluorine-labeled amino acid compound useful for detecting tumors by positron emission tomography (PET).

BACKGROUND ART

The radioactive diagnostic imaging agent is a medicine directly administered to a human body and is a pharmaceutical composition containing a compound labeled with a specific radioisotope as an effective ingredient. The radioactive diagnostic imaging agent enables diagnosis by administering an agent to a subject and detecting a radiation emitted from the compound, followed by imaging based on information obtained from the radiation. The thus-conducted diagnosing method is referred to as nuclear medicine examination, and is effective in diagnosing a variety of diseases including heart disease and cancer. Also, nuclear medicine examination is characteristic in that it has not only high specificity and sensitivity to diseases, but also has an advantage of providing information on the functionality of lesions, compared to other examination techniques.

Compounds which are researched and developed as such radioactive diagnostic imaging agents include 1-amino-3-[$^{18}$F]fluorocyclobutanecarboxylic acid (hereinafter referred to as [$^{18}$F]-FACBC). It is known that [$^{18}$F]-FACBC is taken up into a cell via an amino acid transporter. Thus, [$^{18}$F]-FACBC is expected to be developed as a tumor diagnostic agent since it is largely taken up into tumor cells which are highly proliferative and active in protein synthesis.

In radioactive diagnostic imaging agents, a problem often arises such that compounds decompose by self-radiation during delivery of the agents so as to cause decrease in radiochemical purity due to so-called radiolysis. Particularly, in PET agents for detection of positron nuclides such as $^{18}$F, radiolysis often becomes more problematic since the half-life of the nuclides used therein is shorter than that of nuclides used in SPECT agents for detection of gamma-ray emitting nuclides such as $^{99}$Tc, and thus radioactivity upon shipment must be set larger than SPECT agents, thereby making the resulting radiation energy thereof higher.

For general pharmaceuticals, it is recommended in the guideline of ICH that if impurities in an agent exceed 1.0%, the impurities be subjected to structure determination when the maximum daily dosage of an effective component thereof is as small as not more than 1 mg (Non-Patent Document 1). In most cases, the physical amount of impurities resulting from the radiolysis which may be considered to be one aspect of the decomposition of an agent is as small as about $10^{-12}$ mol, even if it exceeds 1.0%. Since the production amount of impurities such as radioactive decomposed matters is minute, structure determination of the impurities by NMR analysis is difficult even though only determination of molecular weight and presumption of their fragments can be made by mass spectrometry which is excellent in detection sensitivity. Also, it is very difficult to conduct verification as to whether or not the impurities affect effectiveness such as tumor accumulation of the agent.

Therefore, impurities in the radioactive diagnostic imaging agent should be maintained as low as possible, and it is preferable that radiolysis which may cause the production of impurities should also be inhibited as much as possible.

Various methods for inhibiting radiolysis have been examined focusing on application to [$^{18}$F]-fluorodeoxyglucose (hereinafter referred to as [$^{18}$F]-FDG).

International Publication No. WO03/090789 pamphlet discloses a method of reducing the radiolysis of [$^{18}$F]-FDG by adding a weak acid-based buffer to a [$^{18}$F]-FDG solution and an injection prepared by the method (Patent Document 1). Also, International Publication No. WO04/043497 pamphlet discloses adding ethanol to a [$^{18}$F]-FDG solution to obtain a composition of injection which may be reduced in radiolysis of [$^{18}$F]-FDG to improve stability (Patent Document 2).

Japanese Patent Laid-open (Kokai) No. H10-147542 discloses a technique utilizing an organic compound high in physiological acceptability such as monosaccharides, disaccharides, organic acids and salts or esters thereof as a radiation protecting agent (Patent Document 3). In this publication, the organic compound high in physiological acceptability and particularly effective as the radiation protecting agent is defined to have a reaction rate constant with OH radicals, H radicals or hydrated electrons in the range of $1\times10^8$ to $5\times10^{10}$ mol$^{-1}$s$^{-1}$.

International Publication No. WO04/056725 pamphlet discloses a solid-phase synthesis method for $^{18}$F-labeled tracers including [$^{18}$F]-FACBC (Patent Document 4). In this document, it is suggested that radiolysis of $^{18}$F-labeled tracers is reduced by adding ascorbic acid to a composition of injection.

Non-Patent Document 1: ICH HARMONISED TRIPARTITE GUIDELINE, IMPURITIES IN NEW DRUG PRODUCTS Q3B(R2)(page 7)(URL: http://www.pmda.go.jp/ich/q/q3br2_06_7_3e.pdf)

Patent Document 1: International Publication No. WO03/090789 pamphlet

Patent Document 2: International Publication No. WO04/043497 pamphlet

Patent Document 3: Japanese Patent Laid-open (Kokai) No. H10-147542

Patent Document 4: International Publication No. WO04/056725 pamphlet

DISCLOSURE OF THE INVENTION

Problems to be Solved by the Invention

As described above, International Publication No. WO03/090789 pamphlet and International Publication No. WO04/043497 pamphlet disclose conditions for preventing radiolysis of [$^{18}$F]-FDG in the solution. However, these documents only disclose techniques for reducing radiolysis of [$^{18}$F]-FDG only, but do not disclose any technique for reducing radiolysis of a series of radioactive fluorine-labeled amino acid compounds such as [$^{18}$F]-FACBC.

In addition, a technical feature of the invention disclosed in International Publication No. WO03/090789 pamphlet is adding a buffer, that is, increasing radiochemical stability of [$^{18}$F]-FDG at a pH having a buffer action, and it is indicated as Comparative Examples that the radiochemical stability of [$^{18}$F]-FDG does not increase with NaCl which has no buffer action.

Japanese Patent Laid-open (Kokai) No. H10-147542 discloses a technique utilizing an organic compound high in physiological acceptability as a radiation protecting agent for radiopharmaceuticals. However, it is not apparent which compound is selected as the organic compound high in physiological acceptability or how much the compound is added in order to prevent radiolysis of the series of radioactive fluorine-labeled amino acid compounds such as [$^{18}$F]-FACBC.

International Publication No. WO04/056725 pamphlet proposes that the addition of ascorbic acid into a composition of injection reduces the radiolysis of $^{18}$F-labeled tracers. However, it does not contain any concrete disclosure of the use of ascorbic acid as an additive for [$^{18}$F]-FACBC. Also, there is no disclosure as to on what condition it should be used.

The present invention has been made in view of the above circumstances, and aimed at providing a composition comprising a radioactive fluorine-labeled amino acid compound, which can be reduced in radiolysis.

Means for Solving the Problem

As a result of diligent researches, the inventors have found that the radiolysis of [$^{18}$F]-FACBC is reduced dependently upon pH. Particularly, it has been found that when the pH value is not more than 5.9, stability thereof is maintained even if there exist no pharmaceutical additives or buffers that prevent radiolysis.

Therefore, it has been found that decrease of radiochemical purity of the radioactive diagnostic imaging agent can be reduced by keeping the pH of the final agent at 2.0-5.9, and thus the present invention have been completed.

According to one aspect of the present invention, there is provided a radioactive diagnostic imaging agent which comprises a solution containing a radioactive compound represented by the following formula (I) as an effective component:

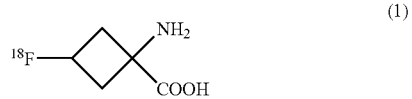

(I)

wherein the solution has a pH value of 2.0-5.9. In a preferable embodiment of the radioactive diagnostic imaging agent according to the present invention, the above solution can have a pH value of 2.0-4.9.

The radioactive diagnostic imaging agent according to the present invention may be one to which a pharmaceutical additive is further added. As pharmaceutical additives, various compounds which are generally accepted as additive compounds can be used, including a pH regulator and a dissolving aid as well as a sugar, a sugar alcohol, a sugar lactone and the like. Preferably, a sugar alcohol can be used.

As the sugar alcohol, one or more compounds selected from the group consisting of erythritol, xylitol, sorbitol and mannitol can be used. Addition amount thereof is not limited as long as it can additionally reduce radiolysis, but is preferably not less than 0.5 µmol/mL, more preferably not less than 1.0 µmol/mL, furthermore preferably not less than 5.0 µmol/mL, and particularly preferably not less than 10.0 µmol/mL. The upper limit of the addition amount needs to be an amount that is acceptable for pharmaceutical additives; for examples, the upper limit as a total daily dose is 200 mg for xylitol, 1.5 g for sorbitol, and 1.2 g for mannitol.

In the radioactive diagnostic imaging agent according to the present invention, radioactive concentration is not particularly limited as long as a sufficient amount of radioactivity can be ensured when used. More specifically, the radioactive concentration in use is preferably 25-125 MBq/mL, and more preferably 25-100 MBq/mL.

In the present specification, compounds acceptable as pharmaceutical additives mean compounds that are approved as pharmaceutical additives in the Japanese Pharmacopoeia, the United States Pharmacopoeia, the European Pharmacopoeia, and so on. In addition, sugar alcohol means a reduced form of a sugar, and sugar lactone means a cyclic ester compound that is derived by intramolecular dehydration condensation of a sugar.

Effect of the Invention

According to the present invention, a pH value of a solution containing a radioactive fluorine-labeled amino acid compound is regulated to 2.0-5.9, and thus a composition of a radioactive fluorine-labeled amino acid compound is provided which is reduced in radiolysis.

BEST MODE FOR CARRYING OUT THE INVENTION

Hereinafter, the most preferable embodiments for the composition of the radioactive fluorine-labeled amino acid compound according to the present invention will be described.

The radioactive diagnostic imaging agent according to the present invention is produced in 4 steps; a step of imparting radioactive fluorine to a precursor (step 1); a step of performing deprotection of the compound to which the radioactive fluorine has been imparted (step 2); a step of performing purification of a solution containing anti-[$^{18}$F]-FACBC after deprotection (step 3); and a step of processing the purified anti-[$^{18}$F]-FACBC solution into a preparation (step 4).

Radioactive fluorine can be obtained by a known method, for example, a method in which H$_2$$^{18}$O enriched water is used as a target and exposed to proton bombardment. In this instance, radioactive fluorine exists in the H$_2$$^{18}$O enriched water used as a target. The H$_2$$^{18}$O enriched water containing radioactive fluorine is allowed to pass through, for example, an anion-exchange resin column so that the radioactive fluorine is adsorbed and collected on the column, thereby being separated from the H$_2$$^{18}$O enriched water. Thereafter, a potassium carbonate solution is allowed to pass through the column to elute the radioactive fluorine, and the eluate is supplemented with a phase transfer catalyst and is evaporated to dryness, thereby activating the radioactive fluorine.

In step 1, the dried radioactive fluorine is dissolved in acetonitrile, and ethyl cis-1-(N-tert-butoxycarbonyl)amino-3-[(trifluoromethyl)sulfonyloxy]-cyclobutanecarboxylate, as a precursor, is added to the acetonitrile solution to allow them to react under heating. As a result, radioactive fluorine is added to the precursor, whereby ethyl trans-1-(N-tert-butoxycarbonyl)amino-3-[18F]fluorocyclobutanecarboxylate is synthesized.

In step 2, ethyl trans-1-(N-tert-butoxycarbonyl)amino-3-[$^{18}$F]fluorocyclobutane carboxylate obtained in step 1 is deprotected to yield a solution containing anti-[$^{18}$F]-FACBC as a target product. In this step, the condition of deprotection is preferably being acidic. For example, hydrochloric acid can be added to a solution containing ethyl trans-1-(N-tert-butoxycarbonyl)amino-3-[$^{18}$F] fluorocyclobutane carboxylate to perform deprotection. The amount of acid to be added needs not be restricted as long as the amount can provide an acidic condition sufficient for the deprotection.

In step 3, purification of the solution containing anti-[$^{18}$F]-FACBC which is obtained in step 2 is performed. The purification process to be used includes various processes such as a liquid-liquid extraction process and a column separation process. For example, a process in which the reaction solution is injected into HPLC to obtain a fraction containing anti-[$^{18}$F]-FACBC can be used. The anti-[$^{18}$F]-FACBC solution can be obtained in this step.

The radioactive diagnostic imaging agent according to the present invention can be obtained by subjecting the anti-[$^{18}$F]-FACBC solution obtained in step 3 to various operations required for making a preparation, including an operation of vaporizing organic solvents, an operation of adding pharmaceutical additives, an operation of adjusting pH, an operation of adjusting radioactive concentration, and an operation of performing sterilization by means of an autoclave, filtration or the like. In this step, it is preferable that the pH value is controlled in the range of 2.0 to 5.9. For this purpose, it is preferable that the pH value is previously controlled in the range of 2.0 to 5.9 in step 3. Also, it is possible that the pH is controlled in the range of 2.0 to 5.9 immediately after the anti-[$^{18}$F]-FACBC solution is obtained. By way of this step 4, a radioactive diagnostic imaging agent can be obtained which contains the anti-[$^{18}$F]-FACBC as an effective ingredient and is adjusted to the solution pH in the range of 2.0 to 5.9.

Meanwhile, the radioactive diagnostic imaging agent according to the present invention should have a radioactivity enabling PET imaging when it is used, and thus the radioactive concentration at the time of production is adjusted to meet that radioactivity. For example, if it has a radioactivity of 1.4 GBq in about 2 mL immediately after production, it will have a radioactivity of 50-225 MBq when it is used, thereby enabling a sufficient PFT imaging for adults.

EXAMPLE

Hereinafter, the present invention is described below in more detail by way of Examples. However, these Examples never limit the scope of the present invention.

Examples 1-16

Comparative Examples 1-5

Relation Between pH and Decrease of Radiochemical Purity

[$^{18}$F] fluoride ion-containing H$_2$$^{18}$O was allowed to pass through an anion-exchange resin column to adsorb and collect [$^{18}$F] fluoride ion on the column. Then, the column was washed with water, and a mixture containing [$^{18}$F] fluoride ion, a potassium carbonate solution and a phase transfer catalyst was obtained in accordance with the conventional method (for example, a method described in the references (Radioisotopes, 50, (2001), p. 205-227; Radioisotopes, 50, (2001), p. 228-256; "Production and quality control of radioactive agents for PET—Handbook of synthesis and clinical use—(2$^{nd}$ edition)", edited by PET Chemistry Workshop).

The obtained mixture was heated in a reaction vessel to evaporate water to dryness, and was subjected to azeotropic distillation with addition of acetonitrile, and a solution of ethyl cis-1-(N-tert-butoxycarbonyl)amino-3-[(trifluoromethyl)sulfonyloxy]-cyclobutane carboxylate in acetonitrile was added thereto. The obtained solution was heated under stirring so as not to evaporate acetonitrile, thereby allowing nucleophilic substitution reaction to proceed to obtain [$^{18}$F] fluorine-labeled compound.

After the reaction vessel was cooled to about 40° C., water for injection was added to the reaction solution for dilution, and the mixture was passed through a reversed phase silica gel column to collect the [$^{18}$F] fluorine-labeled compound. This column was washed, and flashed with a flow of helium gas, and then a 4 mol/L sodium hydroxide solution was filled in the column, followed by closing the column exit. After 3 minutes, the column exit was opened, and an alkali solution was eluted from the column and collected in a vial. This operation was repeated twice, and washed with water, and then the washings were combined with the alkali solution collected as above.

Next, to the solution collected as above, hydrochloric acid was added, and heated to about 60° C. to effect deprotection reaction. The mixture was then passed through an ion retardation resin column, an alumina column and a reversed phase resin column in this order to perform purification and obtain a stock solution of anti-[$^{18}$F]-FACBC. The pH value of the stock solution of anti-[$^{18}$F]-FACBC was adjusted to about 3.5 by previously placing a hydrochloric acid solution in the vessel that received the stock solution of anti-[$^{18}$F]-FACBC.

Radioactivity of the obtained stock solution of anti-[$^{18}$F]-FACBC was measured, and then the stock solution was diluted with a physiological saline solution so as to have a radioactive concentration of about 510 MBq/mL at the time when experiment was initiated (0 hour in Table 2). 2.23 mL of this solution was aliquoted in a vial of 5 mL in volume, and a predetermined amount of a predetermined solution indicated in Table 1 was added thereto, to obtain a sample solution. The radioactive concentration of the sample solutions immediately after preparation was 653-686 MBq/mL.

TABLE 1

The solution added to each sample solution and its pH after adjustment

| | Added solution (addition amount) | pH after adjustment |
|---|---|---|
| Example 1 | 500 mmol/L HCl (40 µL) | 2.00 |
| Example 2 | 500 mmol/L HCl (40 µL), physiological saline solution (40 µL) | 2.05 |
| Example 3 | 100 mmol/L HCl (50 µL) | 2.66 |
| Example 4 | Physiological saline solution (80 µL) | 3.41 |
| Example 5 | Physiological saline solution (50 µL) | 3.46 |
| Example 6 | 11 mmol/L NaOH (70 µL), physiological saline solution (10 µL) | 3.97 |
| Example 7 | 10 mmol/L NaOH (70 µL) | 4.04 |
| Example 8 | 12 mmol/L NaOH (70 µL), physiological saline solution (10 µL) | 4.55 |
| Example 9 | 11 mmol/L NaOH (70 µL) | 4.58 |
| Example 10 | 12 mmol/L NaOH (70 µL) | 4.88 |
| Example 11 | 17 mmol/L NaOH (60 µL), physiological saline solution (20 µL) | 5.03 |
| Example 12 | 13 mmol/L NaOH (70 µL) | 5.11 |
| Example 13 | 15 mmol/L NaOH (70 µL), physiological saline solution (10 µL) | 5.46 |
| Example 14 | 14.3 mmol/L NaOH (60 µL) | 5.54 |
| Example 15 | 17 mmol/L NaOH (70 µL), physiological saline solution (10 µL) | 5.90 |

TABLE 1-continued

The solution added to each sample solution and its pH after adjustment

| | Added solution (addition amount) | pH after adjustment |
|---|---|---|
| Example 16 | 14 mmol/L NaOH (70 µL) | 5.94 |
| Comparative Example 1 | 18.5 mmol/L NaOH (60 µL), physiological saline solution (20 µL) | 6.28 |
| Comparative Example 2 | 14.1 mmol/L NaOH (70 µL) | 6.31 |
| Comparative Example 3 | 16 mmol/L NaOH (80 µL), physiological saline solution (10 µL) | 6.57 |
| Comparative Example 4 | 15 mmol/L NaOH (70 µL) | 6.83 |
| Comparative Example 5 | 17 mmol/L NaOH (80 µL), physiological saline solution (0 µL) | 7.70 |

The sample solution was stored in an electric thermostatic chamber adjusted to 25° C., TLC analysis was performed on the following conditions at the time of initiation of the experiment (0 hour) and 8.5 hours after the initiation of the experiment, and a value of radiochemical purity was calculated in accordance with the following equation (1). Measurement of the radiochemical purity was repeated three times for each sample solution.

TLC Analysis Conditions:
Mobile phase: acetonitrile/water/100% acetic acid=4/1/1
TLC plate: Silica Gel 60F$_{254}$ (trade name, thickness of membrane: 0.25 mm, manufactured by Merck & Co., Inc.)
Mobile length: 10 cm
TLC scanner: Rita Star (manufactured by Raytest) Number of analysis: Three times $$\text{Radiochemical purity (\%)} = \frac{\text{Radioactivity of } [^{18}F] \ FACBC \ \text{peak}}{\text{Total radioactivity on } TLC \ \text{plate}} \times 100 \quad (1)$$

The results are shown in Table 2 and FIG. 1.

TABLE 2

Changes of radiochemical purity and decrease of radiochemical purity of anti-[$^{18}$F]-FACBC solution in different pH

| | pH | Radiochemical purity (%) | | Decrease* (%) |
|---|---|---|---|---|
| | | 0 hour | 8.5 hours | 8.5 hours |
| Example 1 | 2.00 | 99.41 | 99.44 | 0.03 |
| Example 2 | 2.05 | 99.59 | 99.42 | −0.17 |
| Example 3 | 2.66 | 99.38 | 99.33 | −0.05 |
| Example 4 | 3.41 | 99.51 | 99.21 | −0.30 |
| Example 5 | 3.46 | 99.39 | 99.26 | −0.13 |
| Example 6 | 3.97 | 99.48 | 99.02 | −0.46 |
| Example 7 | 4.04 | 99.38 | 99.11 | −0.27 |
| Example 8 | 4.55 | 99.56 | 99.01 | −0.55 |
| Example 9 | 4.58 | 99.35 | 98.98 | −0.37 |
| Example 10 | 4.88 | 99.44 | 99.07 | −0.37 |
| Example 11 | 5.03 | 99.46 | 98.89 | −0.57 |
| Example 12 | 5.11 | 99.51 | 98.93 | −0.58 |
| Example 13 | 5.46 | 99.52 | 99.06 | −0.46 |
| Example 14 | 5.54 | 99.49 | 99.03 | −0.46 |
| Example 15 | 5.90 | 99.51 | 98.86 | −0.65 |
| Example 16 | 5.94 | 99.45 | 98.93 | −0.52 |
| Comparative Example 1 | 6.28 | 99.53 | 98.81 | −0.72 |
| Comparative Example 2 | 6.31 | 99.37 | 98.80 | −0.57 |
| Comparative Example 3 | 6.57 | 99.43 | 98.67 | −0.76 |
| Comparative Example 4 | 6.83 | 99.32 | 98.35 | −0.97 |
| Comparative Example 5 | 7.70 | 99.37 | 97.31 | −2.06 |

*Decrease (%) = (radiochemical purity after 8.5 hours) − (radiochemical purity after 0 hour)

Referring to the relation between the pH and the decrease of radiochemical purity, relatively mild decrease of radiochemical purity was observed with the pH increase from 2.00 to 5.94. The slope based on linear approximation was calculated, and as a result, the slope was −0.145 in the pH range of 2.00-4.88, and was −0.010 in the pH range of 5.03-5.94.

On the other hand, when the pH value was not less than 6.28, sharp decrease of radiochemical purity occurred with the pH increase. The slope based on linear approximation was calculated, and as a result, it was −1.000. This value was about 6.7 times the value in the pH range of 2.00-4.88, and about 100 times the value in the pH range of 5.03-5.94. From these, it was indicated that when the pH value is not less than 6.28, a drastic decrease of radiochemical purity occurs compared with the pH range of 2.00-5.94.

Examples 17-28

Relation Between Mannitol Concentration and Radiochemical Purity at pH Values of 3.44 and 4.78

A stock solution of anti-[$^{18}$F]-FACBC was prepared in the same manner as in Example 1 using [$^{18}$F] fluoride ion-containing H$_2$$^{18}$O. Then, to the prepared anti-[$^{18}$F]-FACBC stock solution, a hydrochloric acid and a physiological saline solution were added so as to have a radioactive concentration of about 500 MBq/mL and a pH value of about 4.8 at the time when experiment was initiated (0 hour in Table 4). 2.23 mL of the obtained solution was aliquoted in a vial of 5 mL in volume, and a mannitol solution or a hydrochloric acid at the concentration shown in Table 3 was added in an amount shown in Table 3 to obtain a sample solution. The radioactive concentration of the sample solutions immediately after preparation was 553-565 MBq/mL.

TABLE 3

Addition amount of mannitol solution in each sample solution

| | pH | Added solution (addition amount) | Mannitol concentration after adjustment (µmol/mL) |
|---|---|---|---|
| Example 17 | 3.44 | 0.83 mg/mL Mannitol solution (50 µL) 40 mmol/L HCl (20 µL) | 0.1 |
| Example 18 | 3.44 | 4.17 mg/mL Mannitol solution (50 µL) 40 mmol/L HCl (20 µL) | 0.5 |
| Example 19 | 3.44 | 8.34 mg/mL Mannitol solution (50 µL) 40 mmol/L HCl (20 µL) | 1.0 |
| Example 20 | 3.44 | 41.72 mg/mL Mannitol solution (50 µL) 40 mmol/L HCl (20 µL) | 5.0 |

TABLE 3-continued

Addition amount of mannitol solution in each sample solution

| | pH | Added solution (addition amount) | Mannnitol concentration after adjustment (μmol/mL) |
|---|---|---|---|
| Example 21 | 3.44 | 83.43 mg/mL Mannitol solution (50 μL) 40 mmol/L HCl (20 μL) | 10.0 |
| Example 22 | 3.44 | 166.87 mg/mL Mannitol solution (50 μL) 40 mmol/L HCl (20 μL) | 20.0 |
| Example 23 | 4.78 | 0.83 mg/mL Mannitol solution (50 μL) | 0.1 |
| Example 24 | 4.78 | 4.17 mg/mL Mannitol solution (50 μL) | 0.5 |
| Example 25 | 4.78 | 8.34 mg/mL Mannitol solution (50 μL) | 1.0 |
| Example 26 | 4.78 | 41.72 mg/mL Mannitol solution (50 μL) | 5.0 |
| Example 27 | 4.78 | 83.43 mg/mL Mannitol solution (50 μL) | 10.0 |
| Example 28 | 4.78 | 166.87 mg/mL Mannitol solution (50 μL) | 20.0 |

The sample solution was stored in an electric thermostatic chamber adjusted to 25° C., and the value of radiochemical purity was calculated in the same manner as in Example 1 at the time of initiation of the experiment (0 hour) and 8.5 hours after the initiation of the experiment. Measurement of the radiochemical purity was repeated three times for each sample solution.

The results are shown in Table 4 and FIG. 2. In the all Examples at the pH values of 3.44 and 4.78, decrease of radiochemical purity was drastically reduced with increase of mannitol concentration, and the reduction effect was saturated at a mannitol concentration of not less than 5.0 μmol/mL.

Also, the decrease of radiochemical purity was more inhibited at both mannitol concentrations at the pH value of 3.44 than 4.78.

From the above results, it was confirmed that the pH value of the solution contributes to radiochemical stability. Also, it was shown that radiolysis can be additionally reduced by adding a mannitol.

TABLE 4

Change of radiochemical purity and decrease of radiochemical purity of anti-[$^{18}$F]-FACBC solution in the presence of mannitol

| | pH | Mannitol Concentration (μmol/mL) | Radiochemical purity (%) 0 hour | Radiochemical purity (%) 8.5 hours | Decrease* (%) 8.5 hours |
|---|---|---|---|---|---|
| Example 17 | 3.44 | 0.1 | 99.38 | 99.10 | −0.28 |
| Example 18 | 3.44 | 0.5 | 99.46 | 99.22 | −0.24 |
| Example 19 | 3.44 | 1.0 | 99.39 | 99.25 | −0.14 |
| Example 20 | 3.44 | 5.0 | 99.47 | 99.42 | −0.05 |
| Example 21 | 3.44 | 10.0 | 99.42 | 99.33 | −0.09 |
| Example 22 | 3.44 | 20.0 | 99.47 | 99.41 | −0.06 |
| Example 23 | 4.78 | 0.1 | 99.39 | 98.93 | −0.46 |
| Example 24 | 4.78 | 0.5 | 99.47 | 99.09 | −0.38 |
| Example 25 | 4.78 | 1.0 | 99.38 | 99.14 | −0.24 |
| Example 26 | 4.78 | 5.0 | 99.45 | 99.30 | −0.15 |
| Example 27 | 4.78 | 10.0 | 99.41 | 99.26 | −0.15 |
| Example 28 | 4.78 | 20.0 | 99.46 | 99.27 | −0.19 |

*Decrease (%) = (radiochemical purity after 8.5 hours) − (radiochemical purity after 0 hour)

Examples 29-31, Comparative Examples 6-8

Relation Between Decrease of Radiochemical Purity and Radioactive Concentration

A stock solution of anti-[$^{18}$F]-FACBC was prepared in the same manner as in Example 1 using [$^{18}$F] fluoride ion-containing H$_2$$^{18}$O. Radioactivity of the obtained stock solution of anti-[$^{18}$F]-FACBC was measured, and diluted and adjusted so as to have a radioactive concentration of 507 MBq/mL and a mannitol concentration of 10 μmol/mL (hereinafter, referred to as standard solution for sample preparation in these Examples and Comparative Examples). 2.23 mL of the obtained standard solution for sample preparation was aliquoted in a vial of 5 mL in volume, and a hydrochloric acid was added thereto so that the pH value was adjusted to 3.94. From this vial, a solution was fractionated in an amount shown in Table 5, and a physiological saline solution was added respectively to make a sample solution of 1 ml in volume.

TABLE 5

Diluting conditions in each sample

| | pH before dilution | Fractionated amount mL | Dilution rate | Radioactive concentration after dilution* MBq/mL |
|---|---|---|---|---|
| Example 29 | 3.94 | 1 | 1 (no dilution) | 573 |
| Example 30 | | 0.5 | 2 | 292 |
| Example 31 | | 0.1 | 10 | 61 |

*Radioactive concentration after dilution was calculated based on the radioactivity measured about 10 minutes before initiation of experiment.

Separately, 2.23 ml of the above prepared standard solution for sample preparation was aliquoted in a vial of 5 ml in volume, and a sodium hydroxide solution was added to adjust the pH value to 7.91. From this vial, a solution was fractionated in an amount shown in Table 6, and a physiological saline solution was added respectively to make a sample solution of 1 mL in volume for use in Comparative Examples 6-8.

TABLE 6

Diluting conditions in each sample

| | pH before dilution | Fractionated amount mL | Dilution rate | Radioactive concentration after dilution* MBq/mL |
|---|---|---|---|---|
| Comparative Example 6 | 7.91 | 1 | 1 (no dilution) | 586 |
| Comparative Example 7 | | 0.5 | 2 | 296 |
| Comparative Example 8 | | 0.1 | 10 | 62 |

*Radioactive concentration after dilution was calculated based on the radioactivity measured about 10 minutes before initiation of experiment.

The sample solution was stored in an electric thermostatic chamber adjusted to 25° C., and the value of radiochemical purity was calculated in the same manner as in Example 1 at the time of initiation of the experiment (0 hour) and 8.5 hours after the initiation of the experiment. Measurement of the radiochemical purity was repeated three times for each sample solution.

The results are shown in Tables 7 and 8. In Examples 29-31, no matter what the radioactive concentration was, decrease of radiochemical purity was hardly observed (Table 7). On the other hand, in both Comparative Examples 6-8, time-course decrease of radiochemical purity was observed, and it was indicated that radiochemical purity tended to decrease with increase of radioactive concentration (Table 8).

From the above results, at the pH value of 3.94, it was confirmed that the decrease of radiochemical purity was significantly reduced at a radioactive concentration of up to 600 MBq/mL.

Also, the decrease of radiochemical purity was enhanced with the increase of radioactive concentration at the pH value of 7.91, and thus it was indicated that the time-course decrease of radiochemical purity of anti-[$^{18}$F]-FACBC was not caused by decomposition of the anti-[$^{18}$F]-FACBC due to lack of chemical stability against the pH, but was caused by decomposition of the anti-[$^{18}$F]-FACBC due to radiolysis by radiation.

TABLE 7

Relation between radiochemical purity and radioactive concentration in samples derived at pH 3.94

| | Radioactive concentration after dilution* MBq/mL | Radiochemical purity (%) | | |
|---|---|---|---|---|
| | | 0 hour | 6.5 hours | decrease |
| Example 29 | 573 | 99.64 | 99.59 | 0.05 |
| Example 30 | 292 | 99.60 | 99.56 | 0.04 |
| Example 31 | 61 | 99.55 | 99.59 | −0.04 |

*Radioactive concentration after dilution was calculated and measured about 10 minutes before initiation of experiment.

TABLE 8

Relation between radiochemical purity and radioactive concentration in samples derived at pH 7.91

| | Radioactive concentration after dilution* MBq/mL | Radiochemical purity (%) | | |
|---|---|---|---|---|
| | | 0 hour | 6.5 hours | decrease |
| Comparative Example 6 | 586 | 99.24 | 97.57 | 1.67 |
| Comparative Example 7 | 296 | 99.33 | 98.01 | 1.32 |
| Comparative Example 8 | 62 | 99.44 | 98.83 | 0.61 |

*Radioactive concentration after dilution was calculated based on the radioactivity measured about 10 minutes before initiation of experiment.

Examples 32-33

Relation Between Addition of Mannitol and Decrease of Radiochemical Purity

A stock solution of anti-[$^{18}$F]-FACBC was prepared in the same manner as in Example 1. The prepared stock solution of anti-[$^{18}$F]-FACBC was diluted with a hydrochloric acid and a physiological saline solution so as to have a radioactive concentration of 568.1 MBq/mL at the predetermined time when the experiment was initiated (0 hour in Table 9) (pH 3.98). This solution was aliquoted in an amount of 2.23 mL as a sample solution (Example 32). Separately, the solution adjusted to 507 MBq/mL was aliquoted in an amount of 2.23 mL, and a mannitol solution was added thereto to prepare a solution adjusted to have a mannitol concentration of 10 μmol/mL for use in the experiment (Example 33).

The sample solution was stored in an electric thermostatic chamber adjusted to 25° C., TLC analysis was performed at the time of initiation of the experiment (0 hour), 2.5 hours later, 4.5 hours later, 6.5 hours later and 8.5 hours later in the same manner as in Example 1, and the value of radiochemical impurity was calculated in accordance with the following equation (2). Measurement of radiochemical impurity was repeated three times for each sample solution.

$$\text{Radiochemical impurity (\%)} = \frac{\text{Radioactiveity of radiochemical impurity}}{\text{Total radioactivity on TLC plate}} \times 100 \quad (2)$$

The results are shown in Table 9. In the sample solution that was not blended with mannitol (Example 32), radiochemical impurity was reduced to 1% or lower at all the time points by virtue of the effect of the pH adjustment. However, a tendency of time-course increase was indicated at the time point until 6.5 hours after initiation of experiment.

On the other hand, in the sample solution that was blended with mannitol (Example 33), no time-course increase of radiochemical purity was observed.

From the above results, it was indicated that blending mannitol enables the increase of radiochemical impurity by radiolysis to be further inhibited. From this, it was confirmed that the effect of stabilization of radiochemical purity was more strengthened by the addition of mannitol.

TABLE 9

Time-course change of radioactive impurity

| | Radiochemical impurity (%) | | | | |
|---|---|---|---|---|---|
| | 0 hour | 2.5 hours | 4.5 hours | 6.5 hours | 8.5 hours |
| Example 32 | 0.52 | 0.73 | 0.90 | 0.98 | 0.95 |
| Example 33 | 0.50 | 0.52 | 0.48 | 0.56 | 0.49 |

INDUSTRIAL APPLICABILITY

The present invention can reduce the radiolysis of radioactive fluorine-labeled amino acid compounds useful as PET agents, and is useful in the field of radiopharmaceuticals.

BRIEF DESCRIPTION OF THE DRAWINGS

FIG. 1 is a graph which shows a relation between the pH and the decrease of radiochemical purity.

FIG. 2 is a graph which shows a relation between the mannitol concentration and the decrease of radiochemical purity.

The invention claimed is:

1. A radioactive diagnostic imaging agent, which comprises a solution of a radioactive fluorine-labeled amino acid compound represented by the following formula (1):

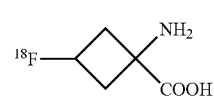

(1)

wherein the solution is free from buffers and has a pH value adjusted to 2.0-4.9 with hydrochloric acid, whereby said radioactive diagnostic imaging agent has reduced radiolysis.

2. The radioactive diagnostic imaging agent according to claim 1, which further comprises a pharmaceutical additive.

3. The radioactive diagnostic imaging agent according to claim 2, wherein the pharmaceutical additive is at least one selected from the group consisting of a sugar alcohol, a sugar and a sugar lactone.

4. The radioactive diagnostic imaging agent according to claim 3, wherein the pharmaceutical additive is a sugar alcohol.

5. The radioactive diagnostic imaging agent according to claim 4, wherein the sugar alcohol is at least one selected from the group consisting of erythritol, xylitol, sorbitol and mannitol.

6. The radioactive diagnostic imaging agent according to claim 4, wherein the sugar alcohol is contained in an amount not less than 0.5 μmol/mL to 20 μmol/mL.

7. The radioactive diagnostic imaging agent according to claim 1, which further comprises a pharmaceutical additive.

8. The radioactive diagnostic imaging agent according to claim 7, wherein the pharmaceutical additive is at least one selected from the group consisting of a sugar alcohol, a sugar and a sugar lactone.

9. A method for stabilizing a solution of a radioactive fluorine-labeled amino acid compound represented by the follow formula (1):

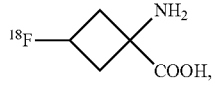
(1)

which comprises maintaining the solution to have a pH value of 2.0-4.9 with hydrochloric acid in the absence of buffers, whereby said radioactive diagnostic imaging agent has reduced radiolysis.

10. A method for producing a radioactive diagnostic imaging agent containing a radioactive fluorine-labeled amino acid compound represented by the following formula (1):

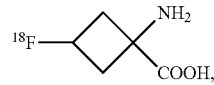
(1)

which comprises:
    a first step of imparting radioactive fluorine to a protected labeling precursor for the compound represented by the above formula (1);
    a second step of performing deprotection of the compound to which the radioactive fluorine has been imparted in the first step;
    a third step of performing purification of the compound which has been deprotected in the second step; and
    a fourth step of processing the compound purified in the third step into a preparation,
in which the compound is maintained in a solution that is free from buffers and has a pH value adjusted to 2.0-4.9 with hydrochloric acid, in the fourth step, whereby said radioactive diagnostic imaging agent has reduced radiolysis.

11. A method according to claim 10, in which the compound is maintained in a solution that is free from buffers and has a pH value of 2.0-4.9, in the third step.

\* \* \* \* \*